US006706408B2

(12) United States Patent
Jelle

(10) Patent No.: US 6,706,408 B2
(45) Date of Patent: Mar. 16, 2004

(54) SILANE COATING COMPOSITION

(75) Inventor: Bruce M. Jelle, Chanhassen, MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

(21) Appl. No.: 10/147,098

(22) Filed: May 16, 2002

(65) Prior Publication Data

US 2003/0215649 A1 Nov. 20, 2003

(51) Int. Cl.$^7$ ................................................. B32B 9/04
(52) U.S. Cl. .................... 428/447; 427/2.1; 427/457; 427/470; 427/487; 428/448; 428/450; 428/451; 428/452; 522/113; 522/127; 522/126; 522/130; 522/151; 522/153; 522/154
(58) Field of Search .................. 427/2.1, 457, 470, 427/487, 489; 428/447, 448, 450, 451, 452; 522/113, 127, 130, 126, 151, 153, 154

(56) References Cited

U.S. PATENT DOCUMENTS

| | | | |
|---|---|---|---|
| 5,414,075 A | | 5/1995 | Swan et al. |
| 5,443,455 A | | 8/1995 | Hergenrother et al. |
| 5,637,460 A | | 6/1997 | Swan et al. |
| 5,714,360 A | | 2/1998 | Swan et al. |
| 5,749,837 A | | 5/1998 | Palermo et al. |
| 5,750,206 A | | 5/1998 | Hergenrother et al. |
| 5,962,161 A | * | 10/1999 | Zucker ........................ 429/142 |
| 6,077,698 A | | 6/2000 | Swan et al. |
| 6,121,027 A | | 9/2000 | Clapper et al. |
| 6,228,390 B1 | * | 5/2001 | Kundel ........................ 424/448 |
| 6,254,634 B1 | | 7/2001 | Anderson et al. |
| 6,278,018 B1 | | 8/2001 | Swan |
| 6,372,813 B1 | | 4/2002 | Johnson et al. ............. 522/114 |

FOREIGN PATENT DOCUMENTS

| | | |
|---|---|---|
| WO | WO 99/01766 | 1/1999 |
| WO | WO 99/08717 | 2/1999 |
| WO | WO 02/13871 A2 | 2/2002 |

OTHER PUBLICATIONS

Jo, S. et al., "Surface modification using silanated poly(ethylene glycol)s," *Biomaterials*, vol. 21, pp. 605–616 (2000).
Zhang, F. et al., "Surface modification of stainless steel by grafting of poly(ethylene glycol) for reduction in protein adsorption," *Biomaterials*, vol. 22, pp. 1541–1548 (2001).

\* cited by examiner

Primary Examiner—Robert Dawson
Assistant Examiner—Marc S. Zimmer
(74) Attorney, Agent, or Firm—Merchant & Gould P.C.

(57) ABSTRACT

An inorganic substrate with two or more coating layers is provided. The first coating layer is attached to the inorganic substrate and includes the polymeric reaction product formed upon hydrolysis of a silane compound having at least two tri($C_1$–$C_3$)alkoxysilyl groups. The second and subsequent coating layers include at least one hydrophilic polymer and at least one photoactivatable cross-linking agent. The inorganic substrate can be a medical device suitable for insertion into the body of a mammal. The coatings are tenacious and not easily removed from the inorganic substrate by abrasion.

43 Claims, No Drawings

SILANE COATING COMPOSITION

TECHNICAL FIELD OF THE INVENTION

The invention provides an inorganic substrate having a first coating layer that includes a silane compound or a reaction product thereof and a second coating layer that includes at least one hydrophilic polymer and at least one photoactivatable cross-linking agent.

BACKGROUND OF THE INVENTION

The properties of the various substrate can be altered through the use of coatings applied to the substrate. For example, medical devices can be covered with one or more coating layers to alter the lubricity of the device, the hydrophobic/hydrophilic nature of the device, the biocompatibility of the device, the attachment of bioactive molecules to the device, and the release of bioactive molecules from the device.

Coating medical devices is particularly challenging. Such devices are often twisted or contorted upon use. The coatings need to adhere sufficiently to the device with minimal cracking or peeling. Further, such coatings typically are thin so that the dimensions and modulus of the device are minimally affected by the presence of the coatings.

SUMMARY OF THE INVENTION

The invention provides an inorganic substrate having at least two coating layers. The first coating layer is attached to the inorganic substrate and contains a silane compound, a hydrolysis reaction product of the silane compound, a polymeric reaction product formed from the hydrolysis reaction product of the silane compound, or a combination thereof. The silane compound has at least two tri($C_1$–$C_3$)alkoxysilyl groups and lacks a sulfide group. The second coating layer is attached to the first coating layer and includes at least one hydrophilic polymer and at least one photoactivatable cross-linking agent. The second layer can also include a photopolymer. One or more additional coating layers can be added having a composition that includes at least one hydrophilic polymer, at least one photoactivatable cross-linking agent, and an optional photopolymer.

Another aspect of the invention provides a method of forming two or more coating layers on an inorganic substrate.

Yet another aspect of the invention provides a medical device having multiple coating layers. A first coating layer is attached to the medical device and contains a silane compound, a hydrolysis reaction product of the silane compound, a polymeric reaction product formed from the hydrolysis reaction product of the silane compound, or a combination thereof. The silane compound has at least two tri($C_1$–$C_3$)alkoxysilyl groups and lacks a sulfide group. The second coating layer is attached to the first coating layer and has at least one hydrophilic polymer and at least one photoactivatable cross-linking agent. The second layer can also include a photopolymer. The medical device can have a third or subsequent coating layer containing at least one hydrophilic polymer, at least one photoactivatable cross-linking agent, and an optional photopolymer.

DETAILED DESCRIPTION OF THE INVENTION

The invention provides an inorganic substrate having at least two coating layers. Another aspect of the invention provides a method of forming two or more coating layers on an inorganic substrate. In particular, the first coating layer is bound to the surface of the inorganic substrate and includes a silane compound, a hydrolysis reaction product of the silane compound, a polymeric reaction product formed from the hydrolysis reaction product of the silane compound, or a combination thereof. The silane compound has at least two tri($C_1$–$C_3$)alkoxysilyl groups. The second coating layer is attached to the first coating layer and includes at least one hydrophilic polymer and at least one photoactivatable cross-linking agent. The second coating layer can also include a photopolymer. The first layer is attached to both the inorganic substrate and the second layer; the first layer is between the inorganic substrate and the second layer.

One or more additional coating layers can be added having a composition that includes at least one hydrophilic polymer, at least one photoactivatable cross-linking agent, and an optional photopolymer. Each subsequent layer is attached to the previous layer. The coating layers are tenacious and not easily removed from the inorganic substrate or from adjacent coating layers by abrasion. The coating layers can cover all or only a portion of the inorganic substrate.

Inorganic Substrate

As used herein, the term "substrate" refers to a support material. The substrate is prepared from an inorganic material. In some embodiments, the inorganic substrate contains a metal. The metal can be, for example, iron, titanium, nickel, chromium, cobalt, tantalum, or alloys thereof. Suitable alloys include stainless steel, nitinol (an alloy of nickel and titanium), and the like. The metal can also be a metal such as, for example, platinum, gold, palladium, iridium, or alloys thereof. In other embodiments, the substrate contains a ceramic material, mineral, or glass. Such substrates can be prepared from silicon carbide, silicon nitride, zirconium, alumina, hydroxyapatite, quartz, silica, and the like.

Some embodiments of the inorganic substrate include medical devices that can be inserted into the body of a mammal. Such medical devices include, but are not limited to, vascular devices such as guidewires, stents, stent grafts, covered stents, catheters, valves, distal protection devices, aneurysm occlusion devices, septal defect closures, and artificial hearts; heart assist devices such as defibrillators, pacemakers, and pacing leads; orthopedic devices such as joint implants and fracture repair devices; dental devices such as dental implants and fracture repair devices; ophthalmic devices and glaucoma drain shunts; urological devices such as penile, sphincter, urethral, ureteral, bladder, and renal devices; and synthetic prostheses such as breast prostheses and artificial organs. The multiple coating layers on the medical device are durable and well suited for applications in which the medical device is subjected to twisting and bending.

Other embodiments of inorganic substrate include non-implanted biomedical devices such as, but are not limited to, diagnostic slides such as gene chips, DNA chip arrays, microarrays, protein chips, and fluorescence in situ hybridization (FISH) slides; arrays including cDNA arrays, and oligonucleotide arrays; chromatographic support materials, cell culture devices, biosensors, and the like.

First Coating Layer

The first coating layer is attached to the inorganic substrate and includes a silane compound, a hydrolysis reaction product of the silane compound, a polymeric reaction product formed from the hydrolysis reaction product of the silane compound, or a combination thereof. The silane compound has at least two tri($C_1$–$C_3$)alkoxysilyl groups. Suitable groups include trimethoxysilyl, triethoxysilyl, and tripropoxysilyl, and combinations thereof. In some embodiments, the silane compound has at least two tri-methoxysilyl groups. The silane is free of other groups that can bind to the inorganic substrate such as a sulfide group.

The silane compound has at least two tri($C_1$–$C_3$) alkoxysilyl groups. Examples of suitable tri($C_1$–$C_3$) alkoxysilyl containing silane compounds include, but are not limited to, bis(trimethoxysilyl)hexane, bis(trimethyoxysilyl) ethane, and bis(trimethoxysilylethyl)benzene. A mixture of the tri($C_1$–$C_3$)alkoxysilyl silane compounds can be used. In some embodiments, the silane compound is bis(trimethoxysilylethyl)benzene.

The silane compound, a hydrolysis reaction product of the silane compound, a polymeric reaction product formed from the hydrolysis reaction product, or a combination thereof can bind to the surface of the inorganic substrate by reacting with oxide or hydroxide groups on the surface of the inorganic substrate. A covalent bond forms between the inorganic substrate and at least one compound in the first coating layer. The inorganic substrate can be treated to generate hydroxide or oxide groups on the surface. For example, the substrate can be treated with a strong base such as sodium hydroxide, ammonium hydroxide, and the like. In the case of a metal, the metal can be subjected to an oxidizing potential to generate oxide or hydroxide sites on the surface of the metal.

Typically, at least some of the tri($C_1$–$C_3$)alkoxysilyl groups undergo hydrolysis. The hydrolysis reaction product of the silane compound can typically polymerize to form a polymeric reaction product. Trimethoxysilyl groups usually undergo hydrolysis and subsequent polymerization more rapidly than either triethoxysilyl or tripropoxysilyl groups. A layer of the resulting polymeric material typically covalently binds to the surface of the inorganic substrate.

Second Coating Layer

The inorganic substrate having a first coating layer is further coated with a second coating layer that includes at least one hydrophilic polymer and at least one photoactivatable cross-linking agent. The second coating layer can also include a photopolymer. The second coating layer is attached to the first coating layer. In some embodiments, at least one photoactivatable cross-linking agent functions to attach the first coating layer to the second coating layer.

A. Hydrophilic Polymer

The hydrophilic polymer can include synthetic polymers, natural polymers, or a combination thereof. The hydrophilic polymer can be a copolymer or a homopolymer. As used herein, the term "homopolymer" refers to a polymer prepared using only one type of monomer and the term "copolymer" refers to a polymer prepared using two or more different monomers. As used herein, the term "hydrophilic" refers to a polymer that is water-loving; typically the polymers swell in the presence of water.

Suitable natural hydrophilic polymers include alginic acid, alginate, heparin, hyaluronic, acid, hyaluronate, polylysine, chitosan, dextran, gelatin, collagen, cellulose, keratin, and the like.

Suitable synthetic hydrophilic polymers can be prepared from acrylic monomers, vinyl monomers, ether monomers, or combinations thereof. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives thereof. Vinyl monomers include, for example, vinyl acetate, vinyl pyrrolidone, vinyl alcohol, and derivatives thereof. Ether monomers include, for example, ethylene oxide, propylene oxide, butylene oxide, and derivatives thereof.

Suitable hydrophilic polymers can include copolymers such as, for example, polymethyl vinyl ether/maleic anhydride copolymers, polyvinyl pyrrolidone/polymethacrylamide copolymers, and polyvinyl pyrrolidone/polyacrylamide copolymers.

In some embodiments the hydrophilic polymer is polyvinyl pyrrolidone.

A mixture of hydrophilic polymers having different molecular weights can be used in the second coating layer. In one embodiment, a first hydrophilic polymer having an average molecular weight of at least about 500 kilodaltons or at least about 800 is combined with a second hydrophilic polymer having an average molecular weight less than about 200 kilodaltons or less than about 100 kilodaltons. For example a first hydrophilic polymer having molecular weight in the range of about 500 to about 5000 kilodaltons, about 600 to about 2000 kilodaltons, or about 600 to about 1000 kilodaltons is combined with a second hydrophilic polymer having an average molecular weight in the range of about 10 to about 100 kilodaltons, about 15 to about 60 kilodaltons, or about 30 to about 60 kilodaltons. Not being bound by theory, it is theorized that the lower molecular weight material can migrate in the second coating layer and improve the lubricity of the second coating layer. As used herein, the term "lubricity" refers to a characterization of the frictional force associated with the coating. A coating with improved lubricity has a lower frictional force.

In some embodiments, only one molecular weight hydrophilic polymer is used in the second coating layer. For example, the second coating layer is prepared using a hydrophilic polymer having an average molecular weight of at least about 500 kilodaltons or at least about 800 kilodaltons. The average molecular weight can be in the range of about 500 to about 5000 kilodaltons, about 600 to about 2000 kilodaltons, or about 600 to about 1000 kilodaltons. Not being bound by theory, it is thought that the absence of a lower molecular weight polymer, such as a polymer having an average molecular weight less than about 200 kilodaltons, can improve the durability of the second coating layer. As used herein, the term "durability" refers to the wear resistance of the polymer coating. A more durable coating is less easily removed by abrasion.

B. Photoactivatable Cross-linking Agent

The second coating layer includes at least one photoactivatable cross-linking agent that can be non-ionic or ionic. The photoactivatable cross-linking agent has at least one latent photoreactive group that can become chemically reactive when exposed to an appropriate actinic energy source. As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules. See, e.g., U.S. Pat. No. 5,002,582, the disclosure of which is incorporated herein by reference.

Photoreactive groups can be chosen to be responsive to various portions of actinic radiation. Typically, groups are chosen that can be photoactivated using either ultraviolet or visible radiation. Suitable photoreactive groups include, for example, azides, diazos, diazirines, ketones, and quinones. The photoreactive groups generate active species such as free radicals such as, for example, nitrenes, carbenes, and excited states of ketones upon absorption of electromagnetic energy.

In some embodiments, the photoreactive group is an aryl ketone, such as acetophenone, benzophenone, anthrone, and anthrone-like heterocycles (i. e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinone such as, for example anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonryl azides (—$SO_2$—N) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$ CO—O—) such as t-butyl alpha diazoacetoacetate.

Other photoreactive groups include the diazirines (—$CHN_2$) such as 3-trifluoromethyl-3-phenyldiazirine; and ketenes CH=C=O) such as ketene and diphenylketene.

Not being bound by theory, it is thought that in embodiments where at least one non-ionic photoactivatable cross-linking agent is used, the non-ionic photoactivatable cross-linking agent has a tendency to migrate towards the interface between the first coating layer and the second coating layer. The tendency to migrate is attributable to the hydrophobic nature and the relatively low molecular weight of the non-ionic photoactivatable cross-linking agent. In such embodiments, the non-ionic photoactivatable cross-linking agent facilitates the attachment of the first coating layer to the second coating layer. For example, the photoactivatable cross-linking agent can abstract a hydrogen atom from an alkyl group on the silane compound, the hydrolysis reaction product of the silane compound, the polymeric reaction product formed from the hydrolysis reaction product of the silane compound, or a combination thereof. A covalent bond can form between the non-ionic photoactivatable cross-linking agent and at least one of the compounds in the first coating layer and at least one of the compounds in the second coating layer.

Any suitable non-ionic photoactivatable cross-linking agent can be used. In one embodiment, the non-ionic photoactivatable cross-linking agent has the formula $CR_1R_2R_3R_4$ where $R_1$, $R_2$, $R_3$, and $R_4$ are radicals that include a latent photoreactive group.

There can be a spacer group between the central carbon atom and the photoreactive group. Suitable spacers include, for example, —$(CH_2O)_n$— where n is an integer of 1 to 4, —$(C_2H_4O)_m$— where m is an integer of 1 to 3, and similar groups. Preferably, the spacer does not have an atom or group oriented such that it competes with binding of the photoreactive groups to the components of the first coating layer or the polymers of the second coating layer.

In one embodiment of the second coating layer, the non-ionic photoactivatable crosslinking agent comprises the tetrakis (4-benzoylbenzyl ether) or the tetrakis (4-benzoylbenzyl ester) of pentaerthyritol. In this aspect of the invention, one or more of the photoreactive groups can react with the compounds in the first coating layer and one or more of the photoreactive groups can react with the hydrophilic polymer in the second coating layer. By reacting the photoactivatable cross-linking agent with compounds in both the first coating layer and the second coating layer, the first coating layer is attached to the second coating layer.

The photoactivatable cross-linking agent can be ionic. In some embodiments, at least one ionic photoactivatable cross-linking agent is included in the second layer. An ionic photoactivatable cross-linking agent tends to cross-link the polymers within the second coating layer and thereby improves the durability of the second coating layer. Any suitable ionic photoactivatable cross-linking agent can be used. In some embodiments, the ionic photoactivatable cross-linking agent is a compound of formula I:

$$X_1—Y—X_2 \qquad (I)$$

where Y is a radical containing at least one acidic group, basic group, or salt thereof. $X_1$ and $X_2$ are each independently a radical containing a latent photoreactive group.

The photoreactive groups can be the same as those described above for a non-ionic photoactivatable cross-linking agent. Spacers, such as those described for the non-ionic photoactivatable cross-linking agent, can be part of $X_1$ or $X_2$ along with the latent photoreactive group. In some embodiments, the latent photoreactive group includes an aryl ketone or a quinone.

The radical Y in formula I provides the desired water solubility for the ionic photoactivatable cross-linking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable cross-linking agent can be anionic depending on the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths, ammonium, protonated amines, and the like.

For example, a compound of formula I can have a radical Y that contains a sulfonic acid or sulfonate group; $X_1$ and $X_2$ contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018, incorporated herein by reference. The counter ion of the salt can be, for example, ammonium or an alkali metal such as sodium, potassium, or lithium.

In other embodiments of formula I, Y is a radical that contains a basic group or a salt thereof. Such Y radicals can include, for example, an ammonium, a phosphonium, or a sulfonium group. The group can be neutral or positively charged depending on the pH of the coating composition. In some embodiments, the radical Y includes an ammonium group. Suitable counter ions include, for example, carboxylates, halides, sulfate, and phosphate.

For example, compounds of formula I can have a Y radical that contain an ammonium group; $X_1$ and $X_2$ contain photoreactive groups that include aryl ketones. Such photoactivatable cross-linking agents include ethylenebis(4-benzoylbenzyldimethylammonium) salt, hexamethylenebis (4-benzoylbenzyldimethylammonium) salt, 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt, 4,4-bis(4-benzoylbenzyl)morpholinium salt, ethylenebis[(2-(4-benzoylbenzyldimethylammonio)ethyl)-4-benzoylbenzylmethylammonium] salt, and 1,1,4,4-tetrakis (4-benzoylbenzyl)piperazinediium salt. See U.S. Pat. No. 5,714,360, incorporated herein by reference. The counter ion is typically a carboxylate ion or a halide. In one embodiment, the halide is bromide.

A single photoactivatable cross-linker or any combination of photoactivatable crosslinking agents can be used in the second coating layer. In some embodiments, at least one nonionic cross-linking agent such as tetrakis (4-benzoylbenzyl ether) of pentaerthyritol can be used with at least one ionic cross-linking agent. For example, at least one non-ionic photoactivatable cross-linking agent can be used with at least one cationic photoactivatable cross-linking agent such as a ethylenebis(4-benzoylbenzyldimethylammonium) salt or at least one anionic photoactivatable cross-linking agent such as 4,5-bis (4-benzoyl-phenylmethyleneoxy)benzene-1,3-disulfonic acid or salt. In another example, at least one nonionic cross-linking agent can be used with at least one cationic cross-linking agent and at least one anionic cross-linking agent. In yet another example, at least one cationic cross-linking agent can be used with at least one anionic cross-linking agent but without a non-ionic cross-linking agent.

C. Photopolymer

In some embodiments, the second coating layer can also include an photopolymer. As used herein, the term "photopolymer" refers to a polymer having one or more attached latent photoreactive groups. The latent photoreactive group is typically pendant from the polymeric portion of the photopolymer. The photoreactive groups can be any of those discussed above as suitable latent photoreactive groups on the photoactivatable cross-linking agent. In some embodiments, the latent photoreactive group is an aryl ketone or a quinone.

The polymeric portion of the photopolymer can be either a homopolymer or a copolymer and typically is hydrophilic.

The monomers used to prepare the polymeric part of the photopolymer can include acrylic monomers, vinyl monomers, ether monomers, or a mixture thereof. Suitable acrylic monomers include, for example, methyl methacrylate, hydroxyethyl methacrylate, hydroxyethyl acrylate, methacrylic acid, acrylic acid, glycerol acrylate, glycerol methacrylate, acrylamide, methacrylamide, or derivatives thereof. Suitable vinyl monomers include, for example, vinyl acetate, vinyl pyrrolidone, vinyl alcohol, or derivatives thereof. Ether monomers can include, for example, ethylene oxide, propylene oxide, butylenes oxide, or derivatives thereof.

In one embodiment of the photopolymer, the polymeric portion is formed by reacting acrylamide, 2-acrylamide-2-methylpropane sulfonic acid, and N-(3-aminopropyl) methacrylamide. In another embodiment, the polymeric portion is prepared by the copolymerization of 1-vinyl-2-pyrrolidone and N-(3-aminopropyl)methyacrylamide. The copolymers are derivatived with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer. The liberated hydrochloric acid is neutralized with an aqueous base solution.

In some embodiments, it is theorized that the photopolymer attaches to the surface of the first coating layer and functions as a scaffold in the second coating layer. The hydrophilic polymer in the second coating layer attaches to the scaffold through reactions involving the photoactivatable cross-linking agent or agents. Cross-linking the hydrophilic polymer to the photopolymer increases the durability of the second coating layer. By attaching to the first coating layer, the photopolymer can improve adhesion between the first coating layer and the second coating layer.

D. Specific Embodiments

In one embodiment of the second coating layer, the second coating layer is formed from a composition including at least one hydrophilic polymer, at least one non-ionic photoactivatable cross-linking agent, at least one ionic photoactivatable cross-linking agent, and an optional photopolymer. The hydrophilic polymer is prepared from monomers that include acrylic monomers, vinyl monomers, ether monomers, or combinations thereof. The non-ionic cross-linking agent includes a compound of formula $CR_1R_2R_3R_4$ where $R_1$, $R_2$, $R_3$, and $R_4$ are radicals containing a latent photoreactive group. The ionic cross-linking agent includes a compound of formula $X_1$—Y—$X_2$ where $X_1$ and $X_2$ are each independently a radical containing a latent photoreactive group and Y is a radical containing at least one acidic group, basic group, or salt thereof. The optional photopolymer contains aryl ketone or quinone groups attached to a polymeric portion. The polymer portion of the photopolymer is prepared from monomers that include vinyl pyrrolidone, acrylamide, methacrylamide, or mixtures thereof.

More specifically, the second coating layer contains a polyvinyl pyrrolidone having an average molecular weight of at least about 500 kilodaltons. The photoactivatable cross-linking agents include a non-ionic compound such as tetrakis (4-benzoylbenzyl ether) of pentaerthyritol, and an ionic compound such as ethylenebis(4-benzoylbenzyldimethylammonium) salt, 4,5-bis(4-benzoyl-phenylmethyleneoxy)benzene-1,3-disulfonic acid or salt, or a mixture thereof. The optional photopolymer has one or more aryl ketone groups attached to a polymeric portion prepared from monomers that include vinyl pyrrolidone.

In another specific example of a suitable second coating layer composition, two hydrophilic polymers are used. One hydrophilic polymer has an average molecular weight of at least about 500 kilodaltons and the other hydrophilic polymer has an average molecular weight less than about 200 kilodaltons. Both hydrophilic polymers are prepared from monomers that include vinyl pyrrolidone. The photoactivatable cross-linking agent is an ionic compound. For example, the ionic photoactivatable cross-linking agent is ethylenebis(4-benzoylbenzyldimethylammonium) salt, 4,5-bis(4-benzoyl-phenylmethyleneoxy)benzene-1,3-disulfonic acid or salt, or a mixture thereof. The optional photopolymer has one or more aryl ketone photoreactive groups attached to a polymer prepared from monomers that include vinyl pyrrolidone.

Third Coating Layer

In another embodiment of the invention, a third coating layer is applied over the second coating layer. Other coating layers can be applied over the third coating layer. The third and subsequent coating layers are typically formed from a composition that includes at least one hydrophilic polymer and at least one photoactivatable cross-linking agent. The third and subsequent coating layers can contain an optional photopolymer.

The hydrophilic polymer, photoactivatable cross-linking agent, and the optional photopolymer included in the third and subsequent coating layers can be the same as those described for the second coating layer.

In some embodiments, the second and third coating layers are prepared from similar compositions. For example, both the second and the third coating layers can include a hydrophilic polymer having an average molecular weight of at least about 500 kilodaltons. The hydrophilic polymer can be prepared from monomers that include, for example, vinyl pyrrolidone. The photoactivatable cross-linking agent includes at least one non-ionic compound such as tetrakis (4-benzoylbenzyl ether) of pentaerthyritol and at least one ionic compound such as ethylenebis(4-benzoylbenzyldimethylammonium) salt, 4,5-bis(4-benzoyl-phenylmethyleneoxy)benzene-1,3-disulfonic acid or salt, or a mixture thereof. The optional photopolymer can contain one or more aryl ketone groups attached to a polymer portion prepared from monomers that include vinyl pyrrolidone, acrylamide, methacrylamide, or mixtures thereof.

In another example of an inorganic substrate coated with three coating layers, the second and third layer coating layers are prepared from different compositions. The second coating layer can be formed from a composition that includes a hydrophilic polymer having an average molecular weight of at least about 500 kilodaltons. The hydrophilic polymer is prepared from monomers that include, for example, vinyl pyrrolidone. The photoactivatable cross-linking agent includes at least one non-ionic compound such as tetrakis (4-benzoylbenzyl ether) of pentaerthyritol, and at least one ionic compound such as ethylenebis(4-benzoylbenzyldimethylammonium) salt, 4,5-bis(4-benzoyl-phenylmethyleneoxy)benzene-1,3-disulfonic acid or salt, or a mixture thereof. The optional photopolymer contains one or more aryl ketone groups attached to a polymer prepared from monomers vinyl pyrrolidone, acrylamide, methacrylamide, or mixtures thereof.

In this example, the third coating layer contains two hydrophilic polymers. One hydrophilic polymer has an average molecular weight of at least about 500 kilodaltons and the other has an average molecular weight less than about 200 kilodaltons. Both hydrophilic polymers are prepared from monomers that include, for example, vinyl pyrrolidone. The photoactivatable cross-linking agent include at least one ionic compound such as, for example, ethylenebis(4-benzoylbenzyldimethylammonium) dibromide, 4,5-bis(4-benzoylphenylmethyleneoxy)benzene-1,3-disulfonic acid dipotassium salt, or a mixture thereof. The third coating layer composition can contain an optional photopolymer having one or more aryl ketone groups attached to a polymer prepared from monomers vinyl pyrrolidone, acrylamide, methacrylamide, or mixtures thereof.

Medical Device

In one embodiment of the invention, the inorganic substrate is a medical device that can be inserted into a mammal. The medical device is made, at least partially, of a metal or other inorganic material and has at least two coating layers. The first coating layer includes a silane compound, a hydrolysis reaction product of the silane compound, a polymeric reaction product formed from the hydrolysis reaction product of the silane compound, or a combination thereof. The silane compound has at least two tri($C_1$–$C_3$)alkoxysilyl groups and lacks a sulfide group. The second coating layer is attached to the first coating layer and includes at least one hydrophilic polymer and at least one photoactivatable cross-linking agent. The second layer can also include a photopolymer.

In one example of this embodiment, the hydrophilic polymer is prepared from monomers that include acrylic monomers, vinyl monomers, ether monomers, or combinations thereof. The photoactivatable cross-linking agent includes at least one compound that is ionic. The optional photopolymer has one or more aryl ketone or quinone groups attached to a polymeric portion. The polymeric portion of the photopolymer is the reaction product of monomers that include vinyl pyrrolidone, acrylamide, methacrylamide, or mixtures thereof.

In a specific example, the hydrophilic polymer is a polyvinyl pyrrolidone having an average molecular weight of at least about 500 kilodaltons and the optional photopolymer has aryl ketone groups attached to a polymeric portion that is prepared from monomers that include vinyl pyrrolidone. The photoactivatable cross-linking agent includes at least one non-ionic photoactivatable cross-linking agent such as tetrakis (4-benzoylbenzyl ether) of pentaerthyritol, at least one ionic photoactivatable cross-linking agent(s) such as ethylenebis(4-benzoylbenzyldimethylammonium) dibromide, 4,5-bis(4-benzoyl-phenylmethyleneoxy) benzene-1,3-disulfonic acid dipotassium salt, or a mixture thereof.

The medical device can include a third coating layer attached to the second coating layer. The third coating layer includes at least one hydrophilic polymer, at least one photoactivatable cross-linking agent, and an optional photopolymer. The third layer is attached to the second layer.

In one embodiment of the third coating layer, the hydrophilic polymer is prepared from monomers that include acrylic monomers, vinyl monomers, ether monomers, or combinations thereof. The photoactivatable cross-linking agent includes an ionic compound. The optional photopolymer has aryl ketone groups attached to a polymeric portion prepared from monomers that include vinyl pyrrolidone, acrylamide, methacrylamide, or mixtures thereof.

In a specific example, the third coating layer contains two hydrophilic polymers, at least one ionic photoactivatable cross-linking agent, and an optional photopolymer. One of the hydrophilic polymers has an average molecular weight of at least about 500 kilodaltons and the other has an average molecular weight less than about 200 kilodaltons. The two different molecular weight hydrophilic polymers are prepared from monomers that include vinyl pyrrolidone. The ionic photoactivatable cross-linking agent includes, for example, ethylenebis(4-benzoylbenzyldimethylammonium) salt, 4,5-bis(4-benzoylphenylmethyleneoxy)benzene-1,3-disulfonic acid salt, or a mixture thereof. The optional photopolymer contains aryl ketone groups attached to a polymeric portion prepared from monomers that include vinyl pyrrolidone.

Method of Coating an Inorganic Substrate

Another aspect of the invention provides a method of forming two or more coating layers on an inorganic substrate. The method involves binding a first coating layer to an inorganic substrate and then binding a second coating layer to the first coating layer. Subsequent coating layers can be attached to the outermost coating layer. The first coating layer includes a silane compound, a hydrolysis reaction product of the silane compound, a polymeric reaction product formed from the hydrolysis reaction product of the silane compound, or a combination thereof. The silane compound has at least two tri($C_1$–$C_3$)alkoxysilyl groups and lacks a sulfide group. The second layer includes at least one hydrophilic polymer and at least one photoactivatable cross-linking agent. The second layer can also include a photopolymer.

The first layer is applied to the inorganic substrate using any suitable coating method. Such methods include, for example, dipping, spraying, brushing, knife coating, and roller coating. The coating is typically applied at room temperature and dried at a temperature less than about 125° C. until all of the water is driven off.

The thickness of the first coating layer it typically less than about 150 μm. In some embodiments, the thickness is about 5 nm to about 80 nm.

The silane compound is generally mixed with a solvent to form a silane coating composition. The concentration of the silane compound in the first coating layer composition is typically less than about 10 volume percent or less than about 1 volume percent or less than about 0.1 volume percent based on the volume of the solution.

In one embodiment, the solvent is a mixture of water and an alcohol, such as methanol, ethanol, n-propanol, or isopropanol. For example, the solvent can be about 0 to 20 volume percent water and about 80 to about 100 volume percent alcohol such as isopropanol.

The second and subsequent coating layers can be applied using any known coating technique. Suitable techniques include, for example, dipping, spraying, brushing, knife coating, or roller coating. The coating is typically applied at room temperature. The coating is dried partially at room temperature and then cured using an appropriate energy source such as ultraviolet light. A third coating layer can be applied over the second layer either before or after the second coating layer has been cured.

EXAMPLES

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. All percentages, or parts, are by volume unless otherwise noted.

Example 1

Coating of a Stainless Steel Flat With Two Layers

To make a first coating layer, a 0.5%, by volume, portion of 1,4-bis(trimethoxysilylethyl)benzene (B2495.6, Lot #2000308, UCT, Bristol, Pa.) was added to 10%, by volume, distilled water and 89.5%, by volume, isopropyl alcohol (IPA). The resulting silane solution was thoroughly mixed to create a final volume of 50 ml.

A metal flat (0.0254 cm×0.5 cm×2.5 cm) of stainless steel (316L, Goodfellow Cambridge Ltd., Huntingdon, England) was placed in a small vessel containing approximately 50 ml of IPA and sonicated in IPA for 20-minutes at 50–60 hz in a Branson 5210RDTH (Branson Ultrasonic Corp., Danbury, Conn.). Next, the metal flat was wiped with IPA followed by sonication for 20 minutes in a 10% Valtron SP2200 (Valtech Corp, Pottstown, Pa.) solution in hot tap water. The metal flat was rinsed in hot tap water to remove most of the detergent, then sonicated for 2 minutes in hot tap water. The metal flat was rinsed in deionized water followed by sonication for 2-minutes in deionized water. As a final preparative step, the metal flat was sonicated for 2-minutes in IPA and followed by drying at room temperature for approximately 2–5 minutes.

A second coating layer is made from a coating solution consisting of Components I/II/III/IV (12/21/1.0/0.06 wt/v, respectively) in 60% (v/v) IPA in deionized water was prepared as follows. Component I was made by the copolymerization of 1-vinyl-2-pyrrolidone and N-(3-aminopropyl)methacrylamide followed by photoderivatization of the polymer using 4-benzoylbenzoyl chloride under Schotten-Baumann conditions e.g., a two phase aqueous/organic reaction system. Component II was made from PVP (K90F, BASF Corp, Germany). Component III, 4,5-bis(4-benzoylphenylmethyleneoxy)benzene-1,3-disulfonic acid disodium salt was made as described in Example 1 of U.S. Pat. No. 6,278,018. Component IV, tetrakis (4-benzoylbenzyl ether) of pentaerythritol, was made as described in Example 1 of U.S. Pat. No. 5,414,075. For example, to make a 100 ml solution, the following components were added to a beaker of 60 mls of stirring IPA in order: 6 mg Component IV, 2100 mg Component II, 1200 mg Component I, and 100 mg Component III. The Components were stirred for 30 minutes, and then 40 mls of deionized water was added.

To apply a first coating layer, a prepared metal flat, as previously described, was dipped into the silane solution and allowed to soak for three minutes. The silane coated metal flat was removed from the silane solution at the rate of 0.05-cm/sec. The silane coated metal flat was dried at room temperature for at least five minutes followed by further drying in an oven (Model No. 1390FM, Sheldon Manufacturing, Inc., Cornelius, Oreg.) for 15 to 20 minutes at 110° C.

To apply a second coating layer, the silane coated metal flat was dip-coated into the coating solution by dipping the metal flat into the solution at a rate of 1 cm /sec., dwelling for 60 seconds, and withdrawing at a rate of 0.05 cm/sec. After removal of the coated metal from the coating solution, it was air-dried for 10 minutes. The coated metal flat was suspended midway between opposed ELC 4000 lamps (Electro-lite Corp,Danbury, Conn.), approximately 40 cm apart, and containing 400 watt mercury vapor bulbs which put out 1.5 mW/sq. cm from 330–340 nm at the distance of illumination. The coated metal flat was rotated and illuminated for four minutes to insure an even cure of the coating.

The presence of a lubricious adherent layer on the metal flat was verified by staining with a 0.35% aqueous solution of Congo Red (Sigma). Extensive washing of Example 1 under a flow of tap water and rubbing the topcoat surface between the thumb and forefinger (approximately 30 seconds) indicated a strongly adherent lubricous topcoat.

Example 2

Coating of a Gold Flat With two Layers

A metal flat (0.0254 cm×0.635 cm×2.0 cm) of gold, nominally 99.95% pure (Johnson-Matthey Precious Metals Division, West Chester, Pa.) was prepared for coating as described in Example 1. The silane and coating solutions were made and applied to the metal flat as described in Example 1.

The presence of a lubricious adherent layer on the metal flat was verified by staining with a 0.35% aqueous solution of Congo Red (Sigma). Extensive washing of Example 2 under a flow of tap water and rubbing the topcoat surface between the thumb and forefinger (approximately 30 seconds) indicated a strongly adherent lubricous topcoat.

Example 3

Coating of a platinum/Iridium Flat With two Layers

A metal flat (0.0254 cm×0.635 cm×2.0 cm) of 90% platinum/10% iridium (Johnson-Matthey Precious Metals Division, West Chester, Pa.) was prepared for coating as described in Example 1. The silane and coating solutions were made and applied to the metal flat as described in Example 1.

The presence of a lubricious adherent layer on the metal flat was verified by staining with a 0.35% aqueous solution of Congo Red (Sigma). Extensive washing of Example 3 under a flow of tap water and rubbing the topcoat surface between the thumb and forefinger (approximately 30 seconds) indicated a strongly adherent lubricous topcoat.

Comparative Example 4

Coating of a Stainless Steel Flat With two Layers

To make a first coating layer, a 0.5% (v/v) portion of 2-(diphenylphosphino)ethyltriethoxysilane (D6110, Lot #20100101, UCT, Bristol, Pa.) was added to 99.5% (v/v) IPA. The solution was thoroughly mixed to create a final volume of 50 ml. A metal flat (0.0254 cm×0.5 cm×2.5 cm) of stainless steel (316L, Goodfellow, Mass.) was prepared and coated with the D6110 silane solution. For a second coating layer, the coating solution as described in Example 1 was applied.

The presence of a lubricious adherent layer on the metal flat was verified by staining with a 0.35% aqueous solution of Congo Red (Sigma). Extensive washing of Comparative Example 4 under a flow of tap water and rubbing the topcoat surface between the thumb and forefinger (approximately 30 seconds) easily removed the lubricous topcoat.

Comparative Example 5

Coating of a Gold Flat With two Layers

A metal flat (0.0254 cm×0.635 cm×2.0 cm) of gold, nominally 99.95% pure (Johnson-Matthey Precious Metals Division, West Chester, Pa.) was prepared for coating as described in Example 1. A silane solution was prepared and coated to the metal flat as described in Comparative Example 4. For a second coating layer, a coating solution was prepared and applied to the metal flat as described in Example 1.

The presence of a lubricious adherent layer on the metal flat was verified by staining with a 0.35% aqueous solution of Congo Red (Sigma). Extensive washing of Comparative Example 5 under a flow of tap water and rubbing the topcoat surface between the thumb and forefinger (approximately 30 seconds) easily removed the lubricous topcoat.

Comparative Example 6

Coating of a Platinum/Iridium Flat With two Layers

A metal flat (0.0254 cm×0.635 cm×2.0 cm) of 90% platinum/10% iridium (Johnson-Matthey Precious Metals Division, West Chester, Pa.) was prepared for coating as described in Example 1. For a first coating layer, a silane solution was prepared and coated to the metal flat as described in Comparative Example 4. For a second coating layer, a coating solution was prepared and applied to the metal flat as described in Example 1.

The presence of a lubricious adherent layer on the metal flat was verified by staining with a 0.35% aqueous solution of Congo Red (Sigma). Extensive washing of Comparative Example 6 under a flow of tap water and rubbing the topcoat surface between the thumb and forefinger (approximately 30 seconds) easily removed the lubricous topcoat.

Comparative Example 7

Coating of a Stainless Steel Flat With two Layers

To make a first coating layer, a 0.5% (v/v) portion of Bis[3-(Triethoxysilyl)propyl]tetrasulfide (B2494, Lot #2000218, UCT, Bristol, Pa.) was added to 99.5% (v/v) IPA. The solution was thoroughly mixed to create a final volume of 50 ml. A metal flat (0.0254 cm×0.5 cm×2.5 cm) of stainless steel (316L, Goodfellow, Mass.) was prepared and coated with the B2494 silane solution. A second coating layer was applied as described in Example 1.

The presence of a lubricious adherent layer on the metal flat was verified by staining with a 0.35% aqueous solution of Congo Red (Sigma). Extensive washing of Comparative Example 7 under a flow of tap water and rubbing the topcoat surface between the thumb and forefinger (approximately 30 seconds) easily removed the lubricous topcoat.

Comparative Example 8

Coating of a Gold Flat With two Layers

A metal flat (of 0.0254 cm×0.635 cm×2.0 cm) of gold (Johnson-Matthey Precious Metals Division, West Chester, Pa.) was prepared for coating as described in Example 1. To make a first coating layer, a silane solution was prepared and coated to the metal flat as described in Comparative Example 7. For a second coating layer, a coating solution was prepared and applied to the metal flat as described in Example 1.

The presence of a lubricious adherent layer on the metal flat was verified by staining with a 0.35% aqueous solution of Congo Red (Sigma). Extensive washing of Comparative Example 8 under a flow of tap water and rubbing the topcoat surface between the thumb and forefinger (approximately 30 seconds) easily removed the lubricious topcoat.

Comparative Example 9

Coating of a Platinum/Iridium Flat With two Layers

A metal flat (0.0254 cm×0.635 cm×2.0 cm) of 90% platinum/10% iridium (Johnson-Matthey Precious Metals Division, West Chester, Pa.) was prepared for coating as described in Example 1. To make a first coating layer, a silane solution was prepared and coated to the metal flat as described in Comparative Example 7. For a second coating layer, a coating solution was prepared and applied to the metal flat as described in Example 1.

The presence of a lubricious adherent layer on the metal flat was verified by staining with a 0.35% aqueous solution of Congo Red (Sigma). Extensive washing of Comparative Example 9 under a flow of tap water and rubbing the topcoat surface between the thumb and forefinger (approximately 30 seconds) easily removed the lubricous topcoat.

Comparative Example 10

Coating of a Stainless Steel Flat With One Layer

A metal flat (0.0254 cm×0.5 cm×2.5 cm) of stainless steel (316L, Goodfellow, Mass.) was prepared and coated with the coating solution used for the second coating layer as described in Example 1.

The presence of a lubricious adherent layer on the metal flat was verified by staining with a 0.35% aqueous solution of Congo Red (Sigma). Extensive washing of Comparative Example 10 under a flow of tap water and rubbing the topcoat surface between the thumb and forefinger (approximately 30 seconds) easily removed the lubricous topcoat.

Comparative Example 11

Coating of a Gold Flat With One Layer

A metal flat (0.0254 cm×0.635 cm×2.0 cm) of gold, nominally 99.95% pure (Johnson-Matthey Precious Metals Division, West Chester, Pa.) was prepared and coated with the coating solution used for the second coating layer as described in Example 1.

The presence of a lubricious adherent layer on the metal flat was verified by staining with a 0.35% aqueous solution of Congo Red (Sigma). Extensive washing of Comparative Example 11 under a flow of tap water and rubbing the topcoat surface between the thumb and forefinger (approximately 30 seconds) easily removed the lubricious topcoat.

Comparative Example 12

Coating of a Platinum/Iridium Flat With One Layer

A metal flat (0.0254 cm×0.635 cm×2.0 cm) of 90% platinum/10% iridium (Johnson-Matthey Precious Metals Division, West Chester, Pa.) was prepared for coating and coated with the coating solution used for the second coating layer as described in Example 1.

The presence of a lubricious adherent layer on the metal flat was verified by staining with a 0.35% aqueous solution of Congo Red (Sigma). Extensive washing of Comparative Example 12 under a flow of tap water and rubbing the topcoat surface between the thumb and forefinger (approximately 30 seconds) easily removed the lubricous topcoat.

I claim:

1. An article comprising:
   (a) an inorganic substrate;
   (b) a first coating layer bound to a surface of the inorganic substrate, said first coating layer comprising a silane compound, a hydrolysis reaction product of the silane compound, a polymeric reaction product formed from the hydrolysis reaction product of the silane compound, or a combination thereof, wherein said silane compound comprises at least two tri($C_1$–$C_3$)alkyoxysilyl groups and lacks a sulfide group; and
   (c) a second coating layer bound to the first coating layer, said second coating layer comprising at least one hydrophilic polymer and at least one photoactivatable cross-linking agent.

2. The article of claim 1, wherein the medical device comprises a vascular device, a heart assist device, an orthopedic device, a dental device, an ophthalmic device, an urological device, or a synthetic prostheses.

3. The article of claim 2, wherein the vascular device comprises a stent, a catheter, a guidewire, a valve, a distal protection device, an aneurysm occlusion device, a septal defect closure, or an artificial heart.

4. The article of claim 1, wherein the inorganic substrate comprises a mineral, glass, or ceramic material.

5. The article of claim 1, wherein the inorganic substrate comprises a metal.

6. The article of claim 1, wherein the inorganic substrate comprises a metal comprising gold, palladium, platinum, iridium, or alloys thereof.

7. The article of claim 1, wherein the inorganic substrate comprises a metal comprising iron, titanium, nickel, chromium, cobalt, aluminum, tantalum, or alloys thereof.

8. The article of claim 1, wherein the inorganic substrate comprises stainless steel, nitinol, or a platinum/iridium alloy.

9. The article of claim 1, wherein the silane compound comprises at least two trimethoxysilyl groups.

10. The article of claim 1, wherein the silane compound comprises bis(trimethoxysilyl)hexane, bis(trimethoxysilyl)ethane, bis(trimethoxysilylethyl)benzene, or a mixture thereof.

11. The article of claim 1, wherein the silane compound comprises bis(trimethoxysilylethyl)benzene.

12. The article of claim 1, wherein the photoactivatable cross-linking agent comprises at least one non-ionic compound having a formula $CR_1R_2R_3R_4$ where $R_1$, $R_2$, $R_3$, and $R_4$ are radicals comprising a latent photoreactive group.

13. The article of claim 12, wherein the latent photoreactive group comprises an aryl ketone or a quinone.

14. The article of claim 12, wherein at least one of $R_1$, $R_2$, $R_3$, and $R_4$ further comprises a spacer group having a formula —$(CH_2O)_n$— where n is an integer of 1 to 4 or —$(C_2H_4O)_m$— where m is an integer of 1 to 3.

15. The article of claim 12, wherein the non-ionic photoactivatable cross-linking agent comprises tetrakis (4-benzoylbenzyl ether) or tetrakis (4-benzoylbenzyl ester) of pentaerythritol.

16. The article of claim 1, wherein the photoactivatable cross-linking agent comprises at least one ionic compound of the formula $$X_1—Y—X_2$$

wherein
   $X_1$ and $X_2$ comprise a radical having a latent photoactivatable group; and Y comprises a radical containing at least one acidic group, a basic group, or a salt thereof.

17. The article of claim 16, wherein Y comprises a sulfonic acid or salt, a carboxylic acid, a phosphonic acid, or a salt thereof.

18. The article of claim 16, wherein the latent photoreactive group comprises an aryl ketone or quinone.

19. The article of claim 16, wherein the photoactivatable cross-linking agent comprises 4,5-bis(4-benzoylphenylmethyleneoxy)benzene-1,3-disulfonic acid; 2,5-bis(4-benzoylphenylmethyleneoxy)benzene-1,4-disulfonic acid; 2,5-bis(4-benzoylmethyleneoxy)benzene-1-sulfonic acid; or N,N-bis[2-(4-benzoylbenzyloxy)ethyl]-2-aminoethanesulfonic acid; or a salt thereof.

20. The article of claim 16, wherein Y comprises an ammonium, sulfonium, or phosphonium group.

21. The article of claim 16, wherein the photoactivatable cross-linking agent comprises ethylenebis(4-benzoylbenzyldimethylammonium) salt, hexamethylenebis (4-benzoylbenzyldimethylammonium) salt, 1,4-bis(4-benzoylbenzyl)-1,4-dimethylpiperazinediium) salt, bis(4-benzoylbenzyl)hexamethylenetetraminediium salt, bis[2-(4benzoylbenzyldimethylammonio)ethyl]-4-benzoylbenzylmethylammonium salt, 4,4-bis(4-benzoylbenzyl)morpholinium salt, ethylenebis[(2-(4-benzoylbenzyldimethylammonio)ethyl)-4-benzoylbenzylmethylammonium] salt, or 1,1,4,4-tetrakis(4-benzoylbenzyl)piperazinediium salt.

22. The article of claim 1, wherein the hydrophilic polymer comprises a natural polymer comprising alginic acid, alginate, heparin, hyaluronic, acid, hyaluronate, polylysine, chitosan, dextran, gelatin, collagen, cellulose, keratin, or a combination thereof.

23. The article of claim 1, wherein the hydrophilic polymer is prepared by reacting monomers comprising acrylic monomers, vinyl monomers, ether monomers, or combinations thereof.

24. The article of claim 1, wherein the hydrophilic polymer is prepared by reacting monomers comprising vinyl pyrrolidone.

25. The article of claim 1, wherein the hydrophilic polymer comprises a polymer having an average molecular weight of at least about 500 kilodaltons.

26. The article of claim 1, wherein the hydrophilic polymer comprises a first hydrophilic polymer having an average molecular weight of at least about 500 kilodaltons and a second hydrophilic polymer having an average molecular weight of less than about 200 kilodaltons.

27. The article of claim 1, wherein the second coating layer further comprises a photopolymer.

28. The article of claim 27, wherein the photopolymer comprises one or more latent photoreactive groups attached to a polymeric portion, the polymeric portion prepared by reacting monomers comprising acrylic monomers, vinyl monomers, ether monomers, or a mixture thereof.

29. The article of claim 28, wherein the photopolymer comprises one or more aryl ketone groups attached to a polymeric portion, the polymeric portion prepared by reacting monomers comprising vinyl pyrrolidone.

30. The article of claim 1, wherein the second coating layer comprises at least one non-ionic photoactivatable cross-linking agent and at least one ionic photoactivatable cross-linking agent.

31. The article of claim 30, wherein at least one non-ionic photoactivatable cross-linking agent comprises tetrakis (4-benzoylbenzyl ether) of pentaerythritol and at least one ionic photoactivatable cross-linking agent comprises ethylenebis(4-benzoylbenzyldimethylammonium) salt, 4,5-bis(4-benzoyl-phenylmethyleneoxy)benzene-1,3-disulfonic acid or salt, or a mixture thereof.

32. The article of claim 1, further comprising a third coating layer bound to the second coating layer, said third coating layer comprising at least one hydrophilic polymer and at least one photoactivatable cross-linking agent.

33. The article of claim 32, further comprising a photopolymer.

34. A method for preparing an article comprising:
(a) binding a first coating layer to an inorganic substrate, said first coating layer comprising a silane compound, a hydrolysis reaction product of the silane compound, a polymeric reaction product formed from the hydrolysis reaction product of the silane compound, or a combination thereof, wherein said silane compound comprises at least two tri($C_1$–$C_3$)alkoxysilyl group and lacks a sulfide group; and
(b) binding a second coating layer to the first coating layer, said second coating layer comprising at least one hydrophilic polymer and at least one photoactivatable cross-linking agent.

35. The method of claim 34, wherein the second coating layer further comprises a photopolymer.

36. The method of claim 34, further comprising binding a third coating layer to the second coating layer, said third coating layer comprising at least one hydrophilic polymer and at least one photoactivatable cross-linking agent.

37. The method of claim 36, wherein the third coating layer further comprises a photopolymer.

38. A medical device comprising:
(a) an inorganic substrate;
(b) a first coating layer bound to a surface of the inorganic substrate, said first coating layer comprising a silane compound, a hydrolysis reaction product of the silane compound, a polymeric reaction product formed from the hydrolysis reaction product of the silane compound, or a combination thereof, wherein said silane compound comprises at least two tri($C_1$–$C_3$)alkoxysilyl groups and lacks a sulfide group; and
(c) a second coating layer bound to the first coating layer, said second coating layer comprising at least one hydrophilic polymer and at least one photoactivatable cross-linking agent.

39. The medical device of claim 38, wherein the second layer further comprises a photopolymer.

40. The medical device of claim 38, further comprising a third coating layer bound to the second coating layer, said third coating layer comprising at least one hydrophilic polymer and at least one photoactivatable cross-linking agent.

41. A medical device suitable for insertion into the body of a mammal, the medical device comprising:
(a) an inorganic substrate comprising a metal:
(b) a first coating layer bound to a surface of the inorganic substrate, said first coating layer comprising a silane compound, a hydrolysis reaction product of the silane compound, a polymeric reaction product formed from the hydrolysis reaction product of the silane compound, wherein said silane compound comprises at least two trimethoxysilyl groups and lacks a sulfide group;
(c) a second layer bound to the first coating layer, said second layer comprising
(i) at least one hydrophilic polymer prepared by reacting monomers comprising vinyl pyrrolidone;
(ii) at least one non-ionic photoactivatable cross-linking agent having a formula $CR_1R_2R_3R_4$ where $R_1$, $R_2$, $R_3$, and $R_4$ are radicals comprising a latent photoreactive group; and (iii) at least one ionic photoactivatable cross-linking agent having a formula $X_1—Y—X_2$ wherein $X_1$ and $X_2$ comprise a radical comprising a latent photoactivatable group; and Y comprises a radical comprising at least one acidic group, basic group, or salt thereof.

42. The medical device of claim 41 wherein the second layer comprises a photopolymer, wherein the photopolymer comprises one or more latent photoreactive groups attached to a polymeric portion, the polymeric portion prepared by reacting monomer comprising vinyl pyrrolidone, acrylamide, methacrylamide, or a mixture thereof.

43. The medical device of claim 41, further comprising a third layer bound to the second coating layer, said third coating layer comprising at least one hydrophilic polymer and at least one photoactivatable cross-linking agent.

* * * * *